United States Patent [19]

Martinez et al.

[11] Patent Number: 5,453,090
[45] Date of Patent: Sep. 26, 1995

[54] METHOD OF STENT DELIVERY THROUGH AN ELONGATE SOFTENABLE SHEATH

[75] Inventors: Susana Martinez, Pembroke Pines; Margaret F. Yoklavich, Miami, both of Fla.

[73] Assignee: Cordis Corporation, Miami Lakes, Fla.

[21] Appl. No.: 203,805

[22] Filed: Mar. 1, 1994

[51] Int. Cl.⁶ .................................................. A61M 31/00
[52] U.S. Cl. .................................................. 604/53; 606/108
[58] Field of Search ................................. 604/11, 14, 52, 604/53, 96, 104, 281; 623/1, 12; 606/191, 194, 198, 108

[56] References Cited

U.S. PATENT DOCUMENTS

| | | | |
|---|---|---|---|
| 3,204,635 | 9/1965 | Voss et al. | 604/14 |
| 3,760,808 | 9/1973 | Bleuer | 604/14 |
| 4,733,665 | 3/1988 | Palmaz. | |
| 4,848,343 | 7/1989 | Wallstén et al. | 606/194 |
| 5,019,090 | 5/1991 | Pinchuk. | |
| 5,037,392 | 8/1991 | Hillstead. | |
| 5,041,126 | 8/1991 | Gianturco. | |
| 5,104,399 | 4/1992 | Lazarus | 623/1 |
| 5,147,385 | 9/1992 | Beck et al.. | |
| 5,158,548 | 10/1992 | Lau et al. | 604/96 |
| 5,192,297 | 3/1993 | Hull. | |
| 5,242,399 | 9/1993 | Lau et al.. | |
| 5,246,421 | 9/1993 | Saab. | |
| 5,290,295 | 3/1994 | Queras et al. | 606/108 |
| 5,312,415 | 5/1994 | Palermo | 606/108 |
| 5,360,401 | 11/1994 | Turnland | 604/96 |
| 5,391,172 | 2/1995 | Williams et al. | 606/108 |

*Primary Examiner*—Corrine Maglione
*Attorney, Agent, or Firm*—Thomas R. Vigil

[57] ABSTRACT

The stent delivery method and apparatus uses an elongate sheath having a rounded or tapered distal end portion which has a central opening and which is constructed in a manner that permits the distal end portion to expand easily. The method comprises the steps of: placing a stent on a balloon catheter or a balloon on a balloon guidewire thereby forming a stent on a balloon assembly; placing the stent on a balloon assembly in the elongate sheath having an elongate axis; pushing the sheath and stent on a balloon assembly to a desired site in the lumen of a vessel; positioning the stent on a balloon assembly at the desired site; withdrawing the sheath from the stent on a balloon assembly causing the distal end portion of the sheath to expand to pass over the stent and leaving the stent and balloon at the desired site in the lumen; expanding the balloon and stent to expand the stent to a desired diameter; collapsing the balloon; and, removing the balloon and the sheath from the lumen. The central opening permits a guidewire tip to extend therethrough.

11 Claims, 2 Drawing Sheets

METHOD OF STENT DELIVERY THROUGH AN ELONGATE SOFTENABLE SHEATH

BACKGROUND OF THE INVENTION

1. Field of the Invention

The present invention relates to a stent delivery method and apparatus including a stent sheath within which the stent mounted on a balloon of a balloon catheter or BOAW is carried. The sheath is constructed in a special manner at its distal end to permit the stent and balloon to be moved out of the sheath distal end, particularly with ejection of a sheath softening fluid into the sheath.

2. Description of the Related Art Including Information Disclosed Under 37 CFR §1.97–1.99

Heretofore various stents, stent delivery methods and stent delivery apparatus have been proposed. Some examples of these previously proposed stent methods and apparatus are disclosed in the following U.S. patents:

| U.S. Pat. No. | Patentee |
| --- | --- |
| 4,140,126 | Choudhury |
| 4,503,569 | Dotter |
| 4,733,665 | Palmaz |
| 4,739,762 | Palmaz |
| 4,762,128 | Rosenbluth |
| 4,848,342 | Kaltenbach |
| 4,886,062 | Wiktor |
| 4,950,227 | Savin et al. |
| 5,019,090 | Pinchuk |
| 5,037,392 | Hillstead |
| 5,041,126 | Gianturco |
| 5,100,429 | Sinofsky et al. |
| 5,108,416 | Ryan et al. |
| 5,147,385 | Beck et al. |
| 5,158,548 | Lau et al. |
| 5,192,297 | Hull |
| 5,246,421 | Saab |

The Choudhury U.S. Pat. No. 4,140,126 discloses a method for performing aneurysm repair in which a prosthetic graft is carried by a catheter to a location of an aneurysm where it is anchored and the catheter is then removed.

The Dotter U.S. Pat. No. 4,503,569 discloses a transluminally placed expandable graft prosthesis which is inserted into a blood vessel in its unexpanded state and then expanded.

The Palmaz U.S. Pat. No. 4,733,665 and the Palmaz U.S. Pat. No. 4,739,762 disclose an expandable intraluminal graft and a method and apparatus for implanting the expandable intraluminal graft with an angioplasty balloon catheter. The graft can be a wire mesh tube or a thin welded tubular member having a plurality of longitudinal extending spaced slots which are parallel to the longitudinal axis of the tubular member.

The Rosenblurb U.S. Pat. No. 4,762,128 discloses a method and apparatus for treating hypertrophy of the prostate gland by inserting a stent with an expansion catheter.

The Kaltenbach U.S. Pat. No. 4,848,342 discloses a rotatable dilatation catheter that comprises a pressure member formed by a coil of wire having open turns which are expandable and which are situated adjacent a distal end of the catheter.

The Wiktor U.S. Pat. No. 4,886,062 discloses an intravascular radially expandable stent and method of implanting same in a blood vessel.

The Savin et al. U.S. Pat. No. 4,950,227 discloses a stent delivery system including a catheter having an expandable portion and a distal sleeve having a proximal margin overlying a distal margin of the stent in its unexpanded state and a proximal sleeve having a distal margin overlying a proximal margin of the stent in its unexpanded state.

The Pinchuk U.S. Pat. No. 5,019,090 discloses a radially expandable endoprosthesis (stent) and the like which is in a sheath having an open distal end. A cylindrical pusher is located within the sheath for pushing out the stent into an area of a lesion in a blood vessel. Alternatively, the stent can be mounted on a balloon of a balloon catheter for being delivered to the area of the lesion.

The Hillstead U.S. Pat. No. 5,037,392 discloses a stent-implanting balloon assembly which includes a balloon having three longitudinal creases whereby, where the balloon is in a deflated state the lateral extent in-cross-section of the balloon is less than the diameter of a stent received thereon.

The Gianturco U.S. Pat. No. 5,041,126 discloses an endovascular stent and delivery system including a balloon on a balloon catheter. The stent has a generally cylindrical envelope formed by a wire which extends in single circles back and forth between connecting loops in a continuous undulating pattern.

The Sinofsky et al. U.S. Pat. No. 5,100,429 discloses an endovascular stent and delivery system including a coiled stent of collagen-based material which is carried on a balloon of a balloon catheter to a stenosed region in an artery.

The Ryan et al. U.S. Pat. No. 5,108,416 discloses a stent introducer system including a stent received on a balloon of a balloon catheter and a stent retaining means located adjacent at least one end of the balloon for retaining the stent in position until the balloon is inflated, whereupon the stent retaining means releases the stent.

The Beck et al. U.S. Pat. No. 5,147,385 discloses a stent and catheter for the introduction of the stent. The stent is a hollow cylindrical structure which becomes plastic and malleable when heated, such as by heating the balloon.

The Lau et al. U.S. Pat. No. 5,158,548 and the Lau et al. U.S. Pat. No. 5,242,399 disclose a method and system for stent delivery including a sheath extending proximally from a coiled wire spring end of a guidewire in a generally conical manner to a generally cylindrical body that extends rearwardly a sufficient distance to cover a balloon of a balloon catheter received on the guidewire and to cover an expandable stent positioned on the balloon.

The Hull U.S. Pat. No. 5,192,297 discloses an apparatus and method for placement and implantation of a stent. A balloon catheter coaxially carries on a distal end portion thereof the radially expandable stent distally of the balloon of the balloon catheter. The catheter and stent are placed in a guiding catheter in such a way that the stent may emanate from the distal end of the guiding catheter for positioning in a vessel followed by the balloon which is then positioned within the stent and expanded.

The Saab U.S. Pat. No. 5,246,421 discloses a sheath through which a balloon dilatation catheter is moved.

SUMMARY OF THE INVENTION

According to the present invention, there is provided a method for delivering a stent to a site in a lumen of a vessel, the method comprising the steps of:

placing a stent on a balloon of a balloon assembly thereby forming a stent on a balloon assembly;

placing the stent on a balloon assembly in an elongate sheath having an elongate axis and having a distal end portion which is made of a warm, liquid softenable material, which reduces in cross-section toward a distal end of the elongate sheath and which has a central opening in the distal end of the sheath;

pushing the sheath and stent on a balloon assembly to the desired site in the lumen of the vessel;

positioning the stent on a balloon assembly at the desired site;

causing the distal end to expand by softening the sheath material with a warm, physiologically compatible liquid;

withdrawing the sheath proximally from the stent on a balloon assembly to cause the distal end portion to expand and to pass over the stent leaving the stent and the balloon at the desired site in the lumen of the vessel;

expanding the balloon and stent to expand the stent to a desired diameter;

collapsing the balloon; and, removing the balloon and the sheath from the lumen.

The central opening permits a guidewire to extend therethrough.

DESCRIPTION OF THE PREFERRED EMBODIMENT(S)

Figure 1:
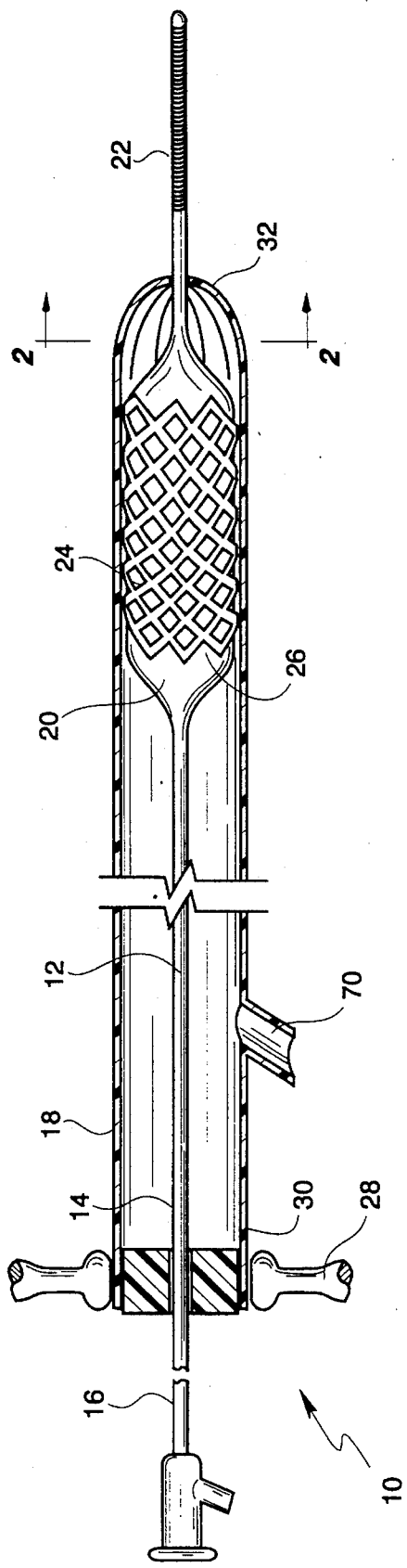
FIG. 1 is a longitudinal partially sectional view of the stent delivery apparatus constructed according to the teachings of the present invention with portions broken away.

Referring now to FIG. 1, there is illustrated therein a stent delivery apparatus or assembly 10 constructed according to the teachings of the present invention. In the illustrated embodiment, the assembly 10 includes a balloon on a wire guidewire 12 including a catheter 14 that extends from a proximal portion 16 thereof which extends into a sheath 18 to a balloon 20 mounted on the catheter 14. The balloon on a wire guidewire 12 further includes a flexible coiled wire spring tip 22 extending distally from the balloon 20 for facilitating tracking of the stent delivery assembly into and through a blood vessel.

A stent 24, which is shown as being of the type disclosed in the Lau et al. U.S. Pat. No. 5,158,548, is mounted on the balloon 20 and received within the sheath 18. It will be understood that the stent 24 can have any number of shapes and can be a metal wire stent or plastic wire stent of the type disclosed in the Gianturco U.S. Pat. No. 5,041,126 or the Pinchuk U.S. Pat. No. 5,019,090.

The stent 24 on the balloon 20 of the balloon on a wire (BOAW) guidewire 12 constitute a stent and balloon assembly 26. Heretofore, such stent on a balloon assembly has been inserted into a blood vessel without being covered by a sheath, such as the sheath 18. When this is done, the stent 24 can cause trauma to the vessel into which it is inserted as it tracks through the vessel.

In view of this fact, it is advisable to place a sheath around the stent 24 when it is inserted into a vessel. The Lau et al. U.S. Pat. No. 5,158,548 shows one form of a sheath which is open at its proximal end but not open at its distal end.

According to the teachings of the present invention, the sheath 18 can be clamped by a hemostat 28 or other clamping mechanism at its proximal end 30 and has a tip or distal end portion 32 which is rounded, tapered or curved, as shown in FIGS. 1 and 3–5 and which is constructed according to the teachings of the present invention.

Figure 2B:
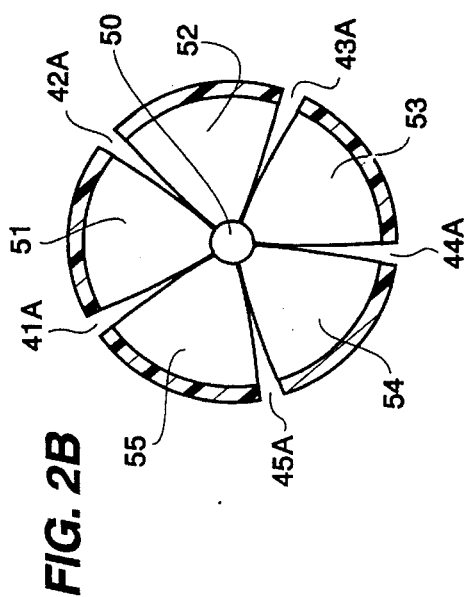
FIG. 2A and 2B are each an enlarged sectional view through the distal end portion of an enclosing sheath, one having weakened area and one having slits and are taken long line 2—2 of FIG. 1.
Figure 2A:
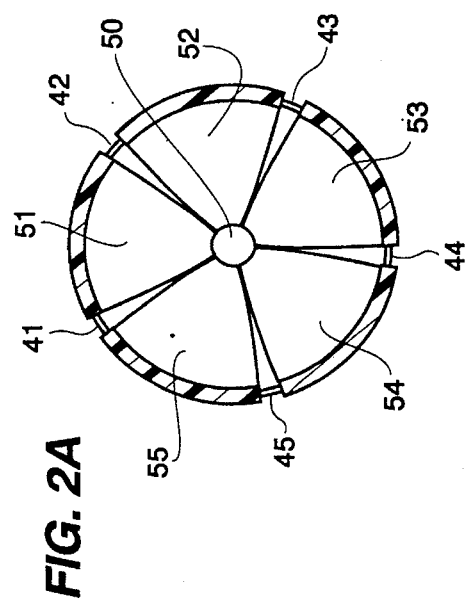

The distal end portion 32 of the sheath 18 which is made of polymer material has weakened areas 41–45 (FIG. 2A), or slits 41A–45A (FIG. 2B), instead of weakened areas, dividing the distal end portion 32 into five sections 51–55. In FIG. 2A and 2B, five weakened areas or slits are shown. It is to be understood, however, that more or less than five lines of weakened area 41–45 (thinned area of material) or slits 41A–45A can be provided in the rounded, tapered or conical distal end portion 32 of the sheath 18.

Then the distal end portion 32 of the sheath 18 has a central opening 50 at the distal end thereof through which the flexible tip 22 can extend for tracking the sheath 18 over the stent on a balloon assembly 26 through a vessel 60.

Figure 3:
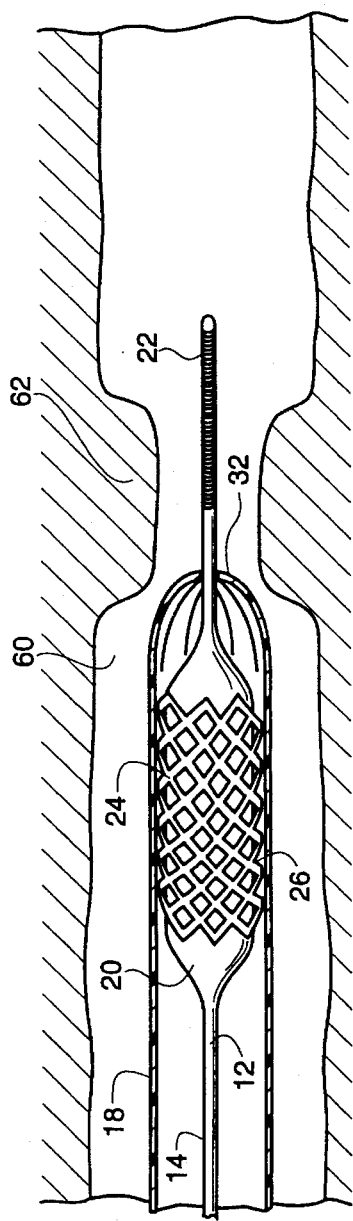
FIG. 3 is a longitudinal sectional view of a portion of a blood vessel having a stenotic lesion and shows a distal portion of the stent delivery apparatus of the present invention positioned just before the lesion.
Figure 4:
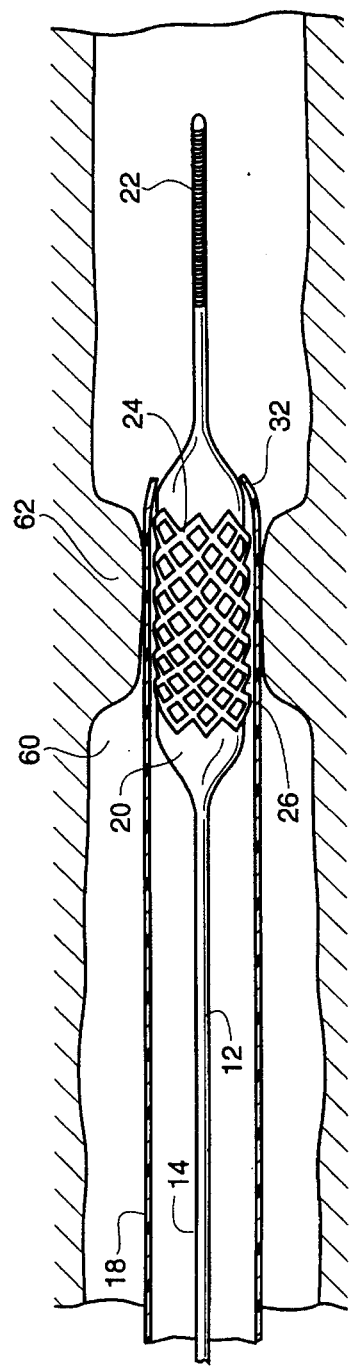
FIG. 4 is a sectional view, similar to the view shown in FIG. 3, of a longitudinal section of the blood vessel having the stenotic lesion but shows the sheath, stent and balloon of the stent delivery system positioned in the area of the stenotic lesion.
Figure 5:
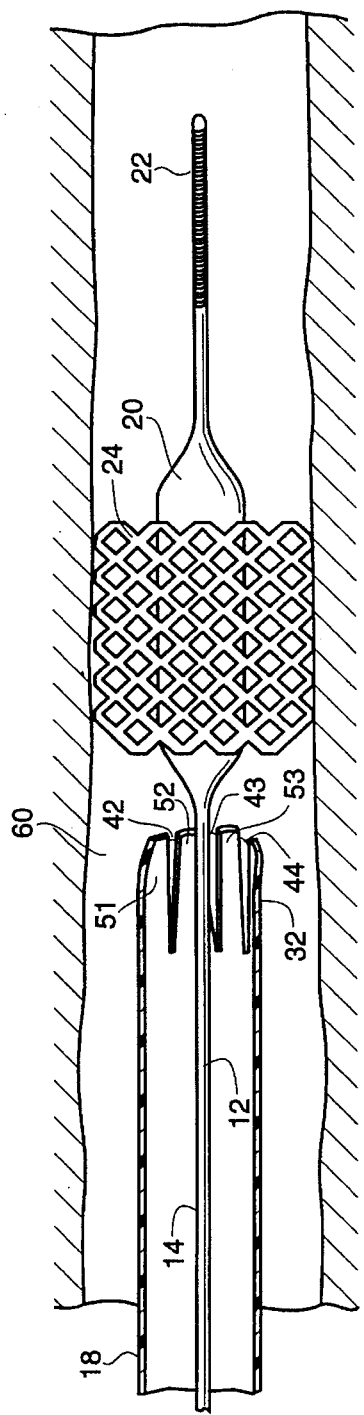
FIG. 5 is a view, similar to the view shown in FIG. 4, but shows the sheath withdrawn or pulled off of the stent on a balloon assembly and after the balloon has been expanded to expand the stent and then collapsed and ready for removal from the vessel.

In the use of the sheath 18 and stent on a balloon assembly 26 forming the stent delivery assembly 10 shown in FIG. 1, the assembly 10 is inserted through the vessel 60 to the site of a stenotic lesion 62, as shown in FIG. 3. Then, the sheath 18, stent 24 and balloon 20 are inserted into the area of stenosis 62, as shown in FIG. 4, and the sheath 18 is pulled rearwardly, as shown in FIG. 5, from its position over the balloon 20 and stent 24. To facilitate flexing of the sections 51–55 in the distal end portion 32 of the sheath 18 between the weakened areas 41–45 or slits 41A–45A, a softening liquid, such as a warm saline solution, is first inserted through an injection port 70 connected to the sheath 18 near the proximal end 30 thereof, as shown in FIG. 1 and through the sheath 18 to the distal end portion 32 thereof. Then, after the distal end portion 32 of the sheath 18 has been softened with the liquid, it can expand and be withdrawn more easily, as shown in FIG. 5. Also, if desired, a softening agent can be included in the softening liquid.

As shown in FIG. 5, after the sheath 18 is withdrawn from the stent on a balloon assembly 24, the balloon 20 is inflated to expand the stent 24, as shown in FIG. 5. Afterwards, the balloon 20 is collapsed to its condition shown in FIG. 5 and the balloon on a wire guidewire (or a balloon catheter) 12, as well as the sheath 18, are withdrawn from the vessel 60.

The sheath 18 is also useful for implanting polymeric stents 24 where the stent must be treated immediately prior to the delivery of the stent 24 with a liquid solution.

Also, it is to be understood that the sheath 18 can be incorporated into a balloon catheter assembly or a balloon on a wire guidewire assembly.

From the foregoing description, it will be apparent that the sheath 18 and the sheath, stent and balloon assembly 10 of the present invention have a number of advantages, some of which have been described above and others of which are inherent in the invention.

For example, the sheath 18 and the sheath, stent and balloon assembly 10 have the following advantages:

1. The smooth rounded atraumatic tip 32 of the sheath 18 allows for dual insertion of the balloon and stent assembly 26 and the sheath 18 at the same time.
2. The sheath 18 protects the stent 24 while tracking through vasculature.
3. The sheath 18 allows for a mini environment which permits bathing of a polymer stent with warm saline.
4. The sheath 18 protects the vasculature from trauma that could be caused by tracking of the stent 24.
5. The sheath 18 minimizes the possibility of dislodgement of the stent 24 from the balloon 20 during tracking of the stent 24 and the balloon 20 through the vasculature.
6. The tip 32 of the sheath 18 can be relaxed when exposed to warm saline or other reactant to facilitate removal of the sheath 18 from the vasculature after the stent 24 and the balloon 20 are placed at the site of a stenotic lesion 62.

Also, from the foregoing description, it will be apparent that modifications can be made to the sheath 18, stent on a balloon assembly 26, i.e., assembly 10, and method for using the sheath 18 of the present invention without departing from the teachings of the invention.

Accordingly, the scope of the invention is only to be limited as necessitated by the accompanying claims.

We claim:

1. A method for delivering a stent to a desired site in a lumen of a vessel, said method comprising the steps of:

placing a stent on a balloon of a balloon assembly thereby forming a stent on a balloon assembly;

placing the stent on a balloon assembly in an elongate sheath having an elongate axis and having a distal end portion which is made of a warm, liquid softenable material, which reduces in cross-section toward a distal end of the elongate sheath and which has a central opening in the distal end of the sheath;

pushing the sheath and stent on a balloon assembly to the desired site in the lumen of the vessel;

positioning the stent on a balloon assembly at the desired site;

causing the distal end of the sheath to expand by softening the sheath material with a warm, physiologically compatible softening liquid;

withdrawing the sheath proximally from the stent on a balloon assembly to cause the distal end portion to expand and to pass over the stent leaving the stent and the balloon at the desired site in the lumen of the vessel;

expanding the balloon and stent to expand the stent to a desired diameter;

collapsing the balloon; and, removing the balloon and the sheath from the lumen.

2. The method of claim 1 wherein said sheath is made of a polymer plastic material.

3. The method of claim 1 wherein said step of causing the distal end portion of the sheath to expand includes the step of placing spaced apart, axially extending slits in the distal end portion.

4. The method of claim 1 wherein said step of causing the distal end portion of the sheath to expand includes the step of placing spaced apart, axially extending, areas of reduced thickness in the wall of the sheath distal end.

5. The method of claim 1 wherein said step of causing the distal end portion of the sheath to expand includes the step of injecting the softening liquid into the sheath to expose the distal end of said sheath to the softening liquid.

6. The method of claim 5 wherein said liquid is a saline solution.

7. The method of claim 5 wherein said softening liquid is a heated liquid.

8. The method of claim 1 wherein said stent is made of a polymer plastic material.

9. The method of claim 1 wherein said stent is made of a metal material.

10. The method of claim 1 wherein said sheath has a rounded distal end.

11. The method of claim 1 wherein said sheath has a conical shaped distal end.

* * * * *